United States Patent
Engberts et al.

[11] Patent Number: 5,853,694
[45] Date of Patent: Dec. 29, 1998

[54] TRANSPORT VEHICLES FOR MACROMOLECULES

[75] Inventors: Jan Bernard Frederik Nicolaas Engberts, Groningen; Anno Wagenaar, Uithuizermeeden; Dirk Hoekstra, Zuidhorn; Irene Van Der Woude, Groningen; Marcel Herman Jozef Ruiters, Zuidhorn, all of Netherlands

[73] Assignees: Stitching Voor DeTechnische Wetenschappen, Utrecht; Rijksuniversiteit Groningen, Groningen; Stichting Scheikundig Ondoerzoek in Nederland, Den Haag, all of Netherlands

[21] Appl. No.: 686,045

[22] Filed: Jul. 24, 1996

[30] Foreign Application Priority Data

Jul. 25, 1995 [NL] Netherlands ............... 1000884

[51] Int. Cl.$^6$ .................. A61K 51/00; A61M 36/14
[52] U.S. Cl. ............... 424/1.21; 424/450; 424/400; 424/149; 546/347; 514/358; 514/975; 514/788
[58] Field of Search .............. 546/347; 424/450, 424/400, 1.49, 1.21; 514/358, 788, 975; 252/312

[56] References Cited

U.S. PATENT DOCUMENTS 4,957,785  9/1990  Huang .

OTHER PUBLICATIONS

Sudhölter et al *JACS* (1980) 102(7) pp. 2467–2469.
Fadhavis et al *JACS* (1982) 47 pp. 2923–2928.
Sudhölter et al *J. Phys. Chem.* (1982) 86 pp. 1908–1913.
Sudholter et al J. Phys. Chem. (1982) 86 pp. 263–271.
Sudholter et al J. Am. Chem. Soc. (1982) 104 pp. 1069–1072.
Nusselder et al J. Org. Chem. (1988) 53 pp. 2423–2426.
Stryer "Biochemistry" (1981) W.H. Freeman and Company New York pp. 207 and 212–213.
N.S. Bodor, "Preparation Of Dihydropyridine–Containing Prodrugs For Brain–Specific Drug Delivery," *Chemical Abstract*, vol. 112:7383s, No. 1, 1990.

E.J.R. Sudholter et al., "Thermotropic Liquid–Crystalline Behavior of Some Single– and Double–Chained Pyridinium Amphiphiles," *Chemical Abstract*, vol. 96:1911b, No. 22, 1982.

J.J.H. Nusselder et al., "Liquid–Crystalline And Thermochromic Behavior Of 4–Subsituted 1–Methylpyridinium Iodide Surfactants," *Chemical Abstract*, vol. 118:202541t, No. 20, 1993.

J.J.H. Nusselder et al., "Relation Between Surfactant Structure And Properties Of Spherical Micelles," *Chemical Abstracts*, vol. 115:240420y, No. 22, 1991.

M. DeCuyper et al., "Exchangeability of Phospholipids Between Anionic, Zwitterionic and Cationic Membranes," *Chemical Abstracts*, vol. 101:165887m, No. 19, 1984.

A.R. Katritzky et al., "Utilization Of Pyridinium Salts As Microsensor Coatings," *Chemical Abstracts*, vol. 111:208460t, No. 22, 1989.

*Primary Examiner*—Paula K. Hutzell
*Assistant Examiner*—Heather A. Bakalyar
*Attorney, Agent, or Firm*—Panitch Schwarze Jacobs & Nadel, P.C.

[57] ABSTRACT

The invention relates to new compounds with the general formula I for use as a tool to introduce macromolecules into cells. The invention further relates to compositions for introducing macromolecules into cells, comprising vesicles formed by at least one compound in a solvent. The macromolecule can be incorporated in the vesicles and/or bound to the vesicles or another aggregate of the new compounds. In a preferred embodiment at least one targeting molecule, for instance a (labelled) antibody, may further be attached to the vesicles.

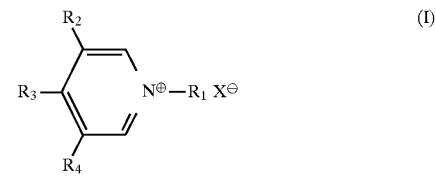

7 Claims, 3 Drawing Sheets

TRANSPORT VEHICLES FOR MACROMOLECULES

FIELD OF THE INVENTION

The present invention relates to new compounds which are capable of introducing macromolecules into eucaryotic cells.

BACKGROUND OF THE INVENTION

The introduction of macromolecules, including DNA, proteins and the like, into eucaryotic cells can be carried out in different ways, for instance by means of transport vehicles. Such vehicles introduce a molecule into the cell, for instance by means of endocytosis. The vehicles may bind, but for instance also encapsulate, the molecules to be transported. In the latter case the vehicles are referred to as vesicles. Known vesicles are liposomes which consist of a bilayer of phospholipids.

Liposomes are for instance used to introduce medicines into the cell. It appeared that liposomes are incorporated into the cell both in vivo and in vitro by means of endocytosis (Nandi, P. K. at al. (1966) J. Biol. Chem. 261:16722; Heath, T. D. (1987) Methods Enzymol. 149:111). This means that the largest portion of the material which is incorporated in the cell will ultimately appear in the lyposomal apparatus, where it will be decomposed. Particularly for substances which have their effect in the cytoplasm or the nucleus this is obviously very disadvantageous.

If the substances to be introduced are hydrophilic it will be difficult to introduce them into liposomes. The main portion of the material remains in the aqueous phase. Particularly in case of expensive substances, like probes and many medicines, this is an obvious disadvantage To prevent that the substances to be introduced into the cell end up in the cell by means of endocytosis, attempts have been made to use fusogenic phospholipids as transport vehicles. The use of fusogenic phospholipids should result in fusion of the from the fusogenic phospholipids formed vesicles with the cell membrane and thus introduce their contents into the cell. However, such attempts have not proven to be very successful because fusogenic liposomes have a strong tendency to mutually merge instead of fusing with the cell membrane (Fonteijn, T. A. A., Ph.D. Thesis (1992)).

One of the most important applications in which molecules are introduced into a cell is transfection of the (eucaryotic) cell with DNA or RNA. Transfection is being used for studying the function and regulation of genes and proteins, but also for the genetic modification of microorganisms, plants and animals. There is a large number of artificial techniques which allow DNA to be introduced into a cell, including DNA-micro-injection, DNA-coprecipitation within inorganic salts or with polycations, DNA-encapsulation in liposomes, and making the cell membrane permeable with the aid of chemical or physical means.

A more recent technique involves the use of cationic amphiphilic molecules as transport vehicles. One of the best-known amphiphiles is the quaternairy ammonium amphiphile DOTMA (N-[1-(2,3-dioleoyloxy)propyl]-N,N,N-trimethylammonium chloride) which in combination with dioleyol phosphatidyl ethanolamine (DOPE), is commercially available with the name Lipofectine®. Both molecules are lipidic(analogues), which form liposomes, which will form complexes with the negatively charged nucleic acids supposedly, the liposomes merge with the plasma membrane and introduce in this way nucleic acids into the cell. However, it could also be done by means of endocytosis. The exact mechanism is yet unknown. With the aid of Lipofectine® the transfection efficiency may be enhanced by a factor of 30 with respect to other known systems, including the classical calcium phosphate precipitation method. However, the disadvantage of Lipofectine® is its toxicity and therefore it may be difficult or not possible to use it in vivo. Therefore, a demand still remains for other and better transfection methods.

SUMMARY OF THE INVENTION

It is the aim of the present invention to provide new cationic amphiphilic compounds, which allow high efficiencies, for the introduction into a cell of nucleic acids and other macromolecules, including for example proteins and medicines.

The aim of the invention is achieved by compounds of general formula I:

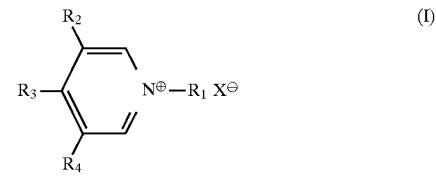

in which:

$R_1$ is a ($C_1$–$C_5$) alkyl, ar (alkyl) or an alkyl group with a cationic fuctional group, like ($C_1$–$C_5$)$N^+$—; or $R_1$ is ($C_1$–$C_5$)$R_5$ in which $R_5$ is a structure with the general formula I;

X is a halide counter ion; chosen from $Cl^-$, $I^-$, $Br^-$; and in which $R_3$ is hydrogen and $R_2$ and $R_4$ are identical or different and are chosen from the group, comprising branched or linear ($C_{10}$–$C_{20}$) alkyl, a mono- or polyunsaturated ($C_{10}$–$C_{20}$) alkenyl, O=C—O-alkyl,

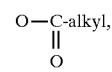

or ar(alkyl), or $R_2$ and $R_4$ are hydrogen and $R_3$ is —CH($R_5$)$_2$ with $R_5$ comprising ($C_{10}$–$C_{20}$) alkyl, mono- or polyunsaturated ($C_{10}$–$C_{20}$) alkenyl, O=C—O-alkyl,

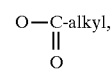

or aralkyl.

DETAILED DESCRIPTION OF THE INVENTION

Figure 1:
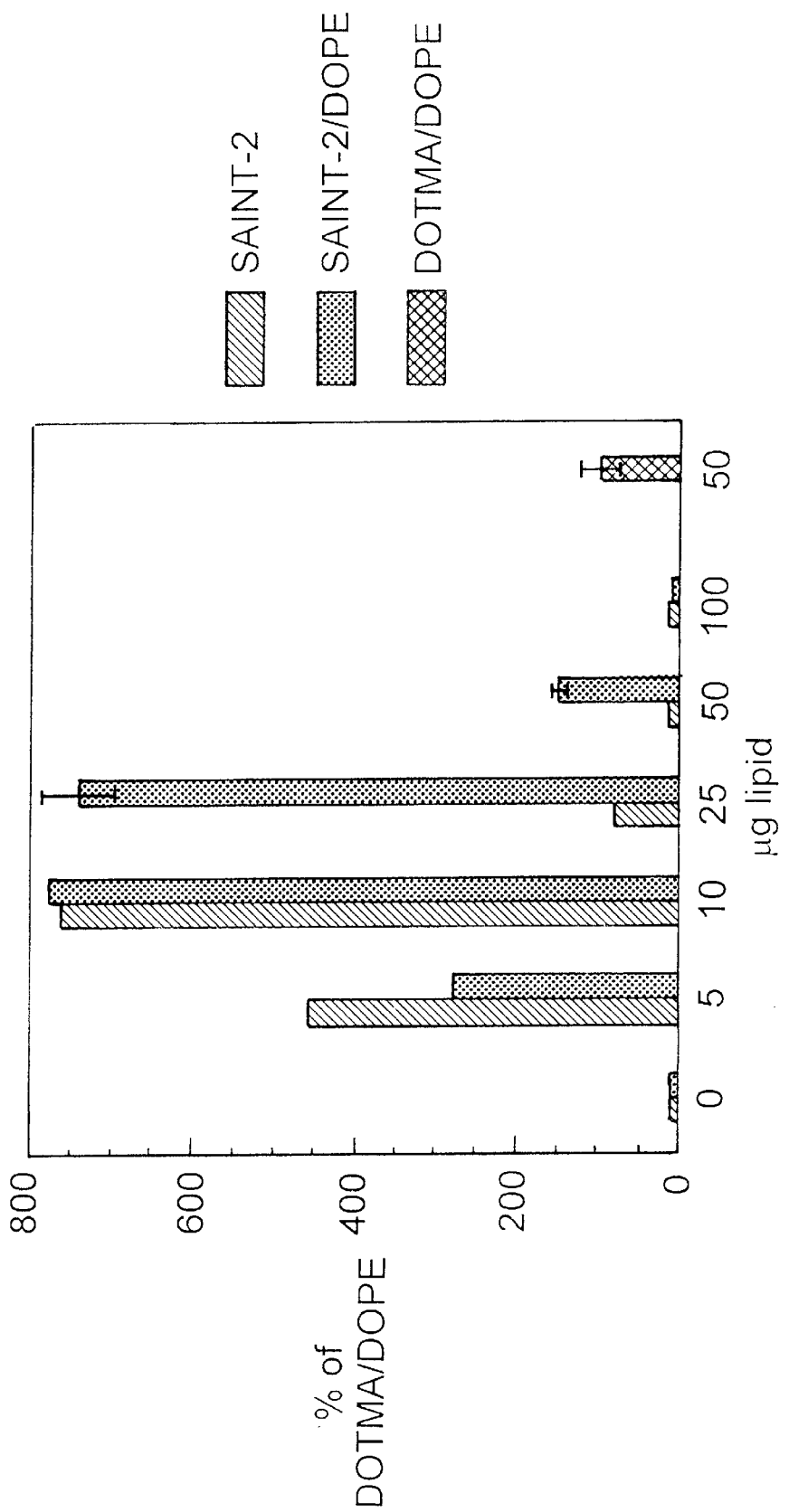
FIG. 1 is a graph showing the relative efficiencies of transfection of COS-7 cells using the synthetic amphiphile SAINT-2 or SAINT-2/DOPE in comparison to transfection efficiency with DOTMA/DOPE.

A particularly advantageous compound according to the invention is 1-methyl-4-(19-cis,cis-hepatritiaconta-9,28-dienyl) pyridinium chloride (SAINT-2). The compounds according to the invention are all based on a pyridine ring, which is at one or two positions substituted by a long (ar) alkyl chain. It has been found that with the amphiphiles according to the invention, and particularly with the compound here referred to as "SAINT-2", a transfection efficiency can be obtained which, dependent on the cell type, is at least eight times higher as that of Lipofectine®.

With SAINT-2/DOPE it also proved to be possible to introduce proteins, particularly gelonine (30 kD), into the cell. Other cell types, particularly Baby Hamster Kidney (BHK) cells, may be transfected. This is impossible with Lypofectine™ for BHK cells. SAINT-2/DOPE yields even better results with BHK cells than Lipofectine™ with COS-7 cells.

The compounds according to the invention may be synthesized in a well-known fashion. The synthesis will be further illustrated in the examples.

The amphiphiles according to the invention may be used in a large number of applications.

The transport into the cell of nucleic acids and their derivatives is of importance for transfection. The aim of transfection is, for instance, to make proteins or to perform research Furthermore, transfected nucleic acids, possibly labelled with streptavidine or radioactively labelled, may be used for in situ hybridisation. A more advanced application is to influence gene expression, for instance blocking of genes by antisense strands. Furthermore, gene expression may also be stimulated. Furthermore, the defect genes may be replaced. The latter two applications are of particular importance in gene therapy.

The advantage of compounds according to the invention is that they, as compared to the known transport vehicles, can be used in much lower, non-toxic concentrations. Probably, they also do not cause an immunologic response.

If DNA and/or RNA are to be introduced into a cell the compounds and the nucleic acids have to be mixed in a certain ratio. It has been found that for the known amphiphiles, including DOTMA, there exists an optimum amphiphile concentration (Felgner, P. L. et al (1987) Proc. Natl. Acad. Sci. USA 84:7413). The transfection efficiency again reduces if a certain amount is exceeded. A comparable situation also holds for the compounds according to the invention.

The cationic amphiphiles according to the invention may also be used to transport negatively charged proteins, including gelonine in particular, into the cell.

The amphiphiles may also be used to transport substances like cytostatics. Lipophilic cytostatics in particular do interact with the compounds according to the invention and may in this way be introduced into the cell very efficiently.

In a preferred embodiment of the invention the transport vehicles may be purposely brought to a specific site by mixing the amphiphiles with a targeting molecule, such as, for instance, an antibody which is directed against an epitope in the neighborhood of the site where the incorporated substance has to exercise its activity. The antibody is preferably coupled to the amphiphilic compound but it may also be coupled, for instance, through a spacer, to the substance to be transported. The antibody may be labeled such as with a radioactive label or a streptavidine label. In order to facilitate the translocations of DNA or other macromolecules across the cell membrane the compounds according to the invention may also be mixed with a phospholipid or with each other.

The present invention will be illustrated in further detail with by means of the accompanying examples which are only serve as an illustration and do not limit the scope of the invention.

EXAMPLES

EXAMPLE 1

Synthesis

Compounds with the general structure formula

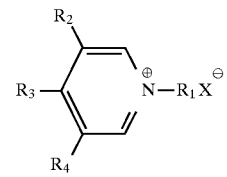

may be divided in a number of groups dependent on their substituents. The synthesis of four of those groups will be given below as an example.

1. 4-Substituted N-alkylpyridinium salts 1.1. Synthesis of 1-methyl-4-(1-octadecylnonadecyl)pyridinium chloride The compound is synthesised according to scheme 1 below as described by E. J. R. Sudhölter in his Ph.D. thesis at the University of Groningen, 1981, page 37.

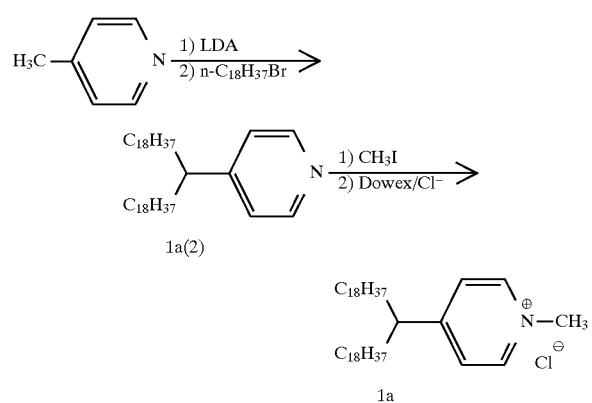

1.2. Synthesis of 1-methyl-4-(19-cis,cis-heptatritiaconta-9,28-dienyl) pyridinium chloride (SAINT-2)

Scheme 2 describes the sequence of the reactions.

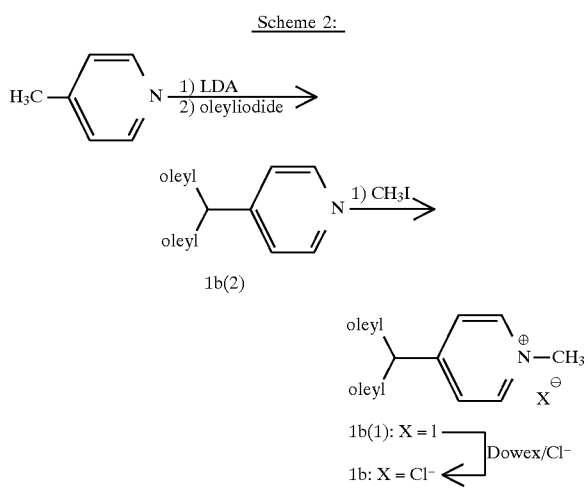

The synthesis has been carried out under nitrogen. 2.226 g (0.022 mol) of di-isopropyl amine was dissolved in 15 ml of dry diethyl ether. Then 13.8 ml (1.6M) n-butyl lithium in n-hexane was added dropwise at 0° C. Subsequently, the mixture was stirred for 10 minutes. This mixture was added dropwise to 0.931 g (0.01 mol) 4-picoline in 10 ml of diethyl ether at −20° C. After this it was stirred for another 30 minutes. The colour of the reaction mixture became deeply orange. Then 7.567 g (0.020 mol) oleyl iodide (85% cis) in 5 ml of diethyl ether was added one portion. The temperature increased to 0° C. while stirring, Subsequently, the mixture was stirred during one night at room temperature. The next day 100 ml of diethyl ether was added to the reaction mixture and subsequently 40 ml of $H_2O$. The organic layer was separated and washed with 3 portions of 30 ml $H_2O$. The ether layer was dried on $Na_2SO_4$, filtered and condensed. The residu (5.9 g) is a viscous brown oil which was purified over a column of 100 g neutral $Al_2O_3$ (act. 2–3). As eluent a mixture of n-hexane-diethyl ether (8:2) was used. 4.32 g (0.0073 mol) 4-(19-cis,cis-heptatritiaconta-9, 28-dienyl)pyridine was obtained (intermediate 1b2, yield 73%).

NMR data: $^1H$ NMR($CDCl_3$): δ 0.89 (t, 6H); 1.27 (chain, 52H); 2.0 (m, 8H); 2.43 (tr. 1H); 5.34 (m, 4H); 7.06 (d, $J_{H,H}$=6 Hz, 2H); 8.49 (d, $J_{H,H}$=6 Hz, 2H). $^{13}C$ NHR: δ 14.0 ($CH_3$); 22.6; 27.1; 27.3; 29.1; 29.2; 29.4; 29.5; 29.6; 29.7; 31.8; 36.1 ($CH_2$-chain); 45.5 (CH); 123.1 (CH) 129.7 (CH); 129.8 (CH); 149.5 (CH); 155.3 (C).

1.527 g (0.0025 mol) of intermediate 1 was dissolved in 10 ml of acetone. Subsequently, 2 ml of methyl iodide was added and the mixture was boiled for 3 hours. After evaporation of the solvent a light yellow brown viscous oil was obtained with a yield of 0.8 g (intermediate 1b1, yield 97%).

NMR data: $^1H$ NMR($CDCl_3$): δ 0.85 (t, 6H); 1.23 (chain, 44H); 1.55 (m, 4H); 1.73 (m, 4H); 2.00 (m, 8H); 2.77 (m, 1H); 4.7 (2, 3H); 5.31 (m, 4H); 7.74 (d, $J_{H,H}$=6.7 Hz, 2H); 9.31 (d, $J_{H,H}$=6.7 Hz, 2H). $^{13}C$ NMR: δ 13.9 ($CH_3$); 22.4; 26.9; 27.2; 28.9; 29.1; 29.3; 29.4; 29.5; 31.6; 35.4 ($CH_2$-chain); 46.4 (CH); 48.3 (N-$CH_3$); 126.8 (CH); 129.5 (CH); 129.7 (CH); 144.9 (CH); 167.1 (C).

0.4 g (0.00054 mol) of intermediate 2 was dissolved in 3 ml of methanol and this solution was eluted with methanol over a Dowex column (1*8, 200–400 mesh Cl⁻ form). The compound 1b was obtained as a viscous oil in a yield of 0.319 g (0.00049 mol 92%).

NMR data: $^1H$ NMR($CDCl_3$): δ 0.87 (t, 6H); 1.26 ($CH_2$-chain, 44H); 1.57 (m, 4H); 1.75 (m, 4H); 2.00 (m, 8H); 2.77 (m, 1H); 4.77 (s, 3H); 5.32 (m, 4H); 7.15 (d, $J_{H,H}$=6.2 Hz, 2H); 9.50 (d, $J_{H,H}$=6.2 Hz, 2H).

1.3. Synthesis of 1-(1-butyl-N,N,N-trimethyl ammonium)-4-(17-tritacontanyl) pyridinium chloride.

This compound was synthesized according to scheme 3 below.

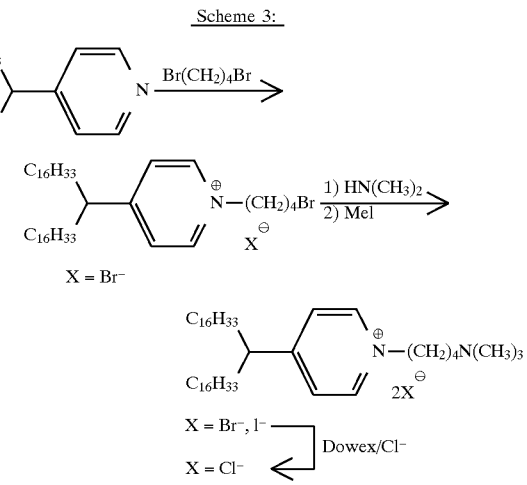

2. 3,5-Disubstituted-N-alkylpyridinium salts

The general synthesis according to scheme 4 below was described in the literature by Sudhölter (vide supra) and Wang et al., J. org. Chem. 42, 1286 (1977).

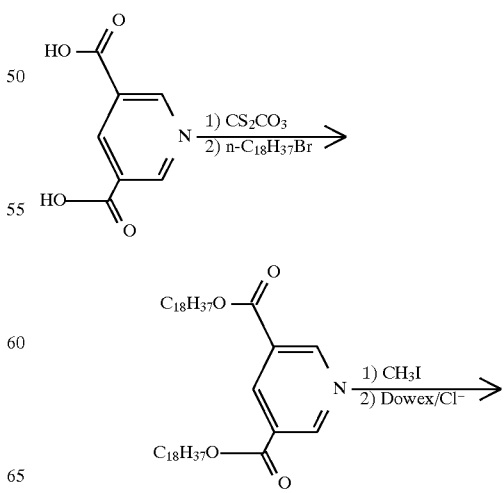

-continued
Scheme 4:

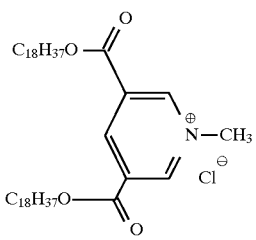

2.1. 1-methyl-3,5-dicarbo-N-octadecyloxy) pyridinium chloride

This compound was synthesized according to scheme 4.

NMR data: $^1$H NMR(CDCl$_3$): δ 0.85 (t, 6H); 1.30 (chain, 64H); 4.40 (t, 4H); 5.03 (s, 3H); 9.20 (t, 1H); 10.00 (d, 2H).

3. 4-Substituted-N-alkyl pyridinium salts

The synthesis was described by F. J. A. Hundscheid and J. B. F. K. Engberts, J. Org. Chem. 49, 3088 (1984).

3.1. 1-Methyl-4((-n-hexadecyloxy)carbonyl) pyridinium iodide

The synthesis of this compound and its characterisation are described by Hundscheid and Engberts (vide supra)).

NMR data: $^1$H NMR(CDCl$_3$): δ 0.9 (t, 3H); 1.25 (m, 28H); 4.35 (t, 2H); 4.70 (s, 3H); 8.35 (d, 2H); 9.35 (d, 2H).

4. 4-Substituted-N-aralkyl pyridinium salts

4.1. 1-(3-phenyl-1-propyl)-4-n-dodecylpyridinium iodide

The compound was synthesized by boiling a mixture of 2.26 g (9.2 mmol) 1-iodo-3-phenyl propane and 2,57 g (10.0 mmol) 4-n-dodecylpyridine in 35 ml of dry acetone for 16 hours. The solvent was evaporated and the yellow solid substance was recrystallized from THF/ether. The yield is 3.06 g (6.2 mmol), melting point 79.0°–80.0° C.

NMR data: $^1$H NMR(CDCl$_3$): δ 0.83 (t, 3H); 1.21 (chain, 20H); 1.61 (m, 2H); 2.36 (m, 2H); 2.78 (m, 2H); 4.89 (t, 2H); 7.05–7.20 (m, 5H); 7.73 (d, 2H); 9.30 (d, 2H).

EXAMPLE 2

Formation of unilamellar vesicles

A suitable amount of lipid was dried under N$_2$(g). In case of combinations of substances these are first mixed and then dried. The lipid film layer is subsequently dried further under vacuum. The lipids are then suspended, vortexed and subsequently sonicated in a suitable volume of water until the solution is clear.

EXAMPLE 3

Transfection of eucaryotic cells by compounds according to the invention

DNA and unilamellar vesicles, as prepared in Example 2, are both brought into Hepes buffered saline (HBS, pH 7.4; both 0.5 ml) and subsequently mixed. The DNA/amphiphile complex is directly formed. In a typical transfection experiment 1 μg of DNA and 7.5–10 μg of the amphiphile SAINT-2 (1-methyl-4-(19-cis,cis-heptatritia contadienyl-9-28) pyridinium chloride) or 1 μg of DNA and 10–15 μg of total amphiphile (SAINT-2/DOPE 1:1) is used.

Cells in six-well plates, which are cofluent by 70–80%, are washed twice with 1 ml of HBS and subsequently 1 ml of the DNA/amphiphile complex was added per well. The cells were incubated during 4 hours at 37° C. after which 1 ml Dulbecco Modified Eagle Medium (DMEM) supplemented with 10% Foetal Calf Serum (FCS) was added. After an incubation of 16 hours at 37° C. the medium was exchanged by 2 ml fresh DMEM with 10% FCS. After a subsequent incubation of 28 hours at 37° C. the cells were gathered. The cells were washed twice with a phosphate buffered saline (PBS) and scraped in 300 μl 1×lysis buffer (Promega). The scraped cells were incubated for 10 minutes at 56° C. and subsequently centrifuged at maximum speed for two minutes at room temperature. On the supernatant an enzyme determination (CAT-assay) and a protein determination (Lowry) were carried out.

100 μl of the cell extract was incubated together with 3 μl $^{14}$C-chloramphenicol (25 mCi/l), 5 μl N-butyryl-CoA (2 mg/ml) and 17 μl 0.25M Tris.HCL (pH 8.0) during 90 minutes at 37° C. The reaction was stopped by adding 0.3 ml of mixed xylenes (Aldrich). The samples were vortexed for 30 seconds and subsequently centrifuged at maximum speed for 3 minutes at room temperature. The organic phase was again extracted with 0.1 ml 0.25M Tris.HCL, vortexed for 30 seconds and centrifuged for 3 minutes. 4 ml of counting fluid was added to 0.2 ml of the organic phase and the radio activity was measured.

It was found that transfection of COS-7 cells with the new amphiphile (SAINT-2 and SAINT/DOPE) is eight times more efficient that with DOTMA/DOPE vesicles (see FIG. 1).

Figure 2:
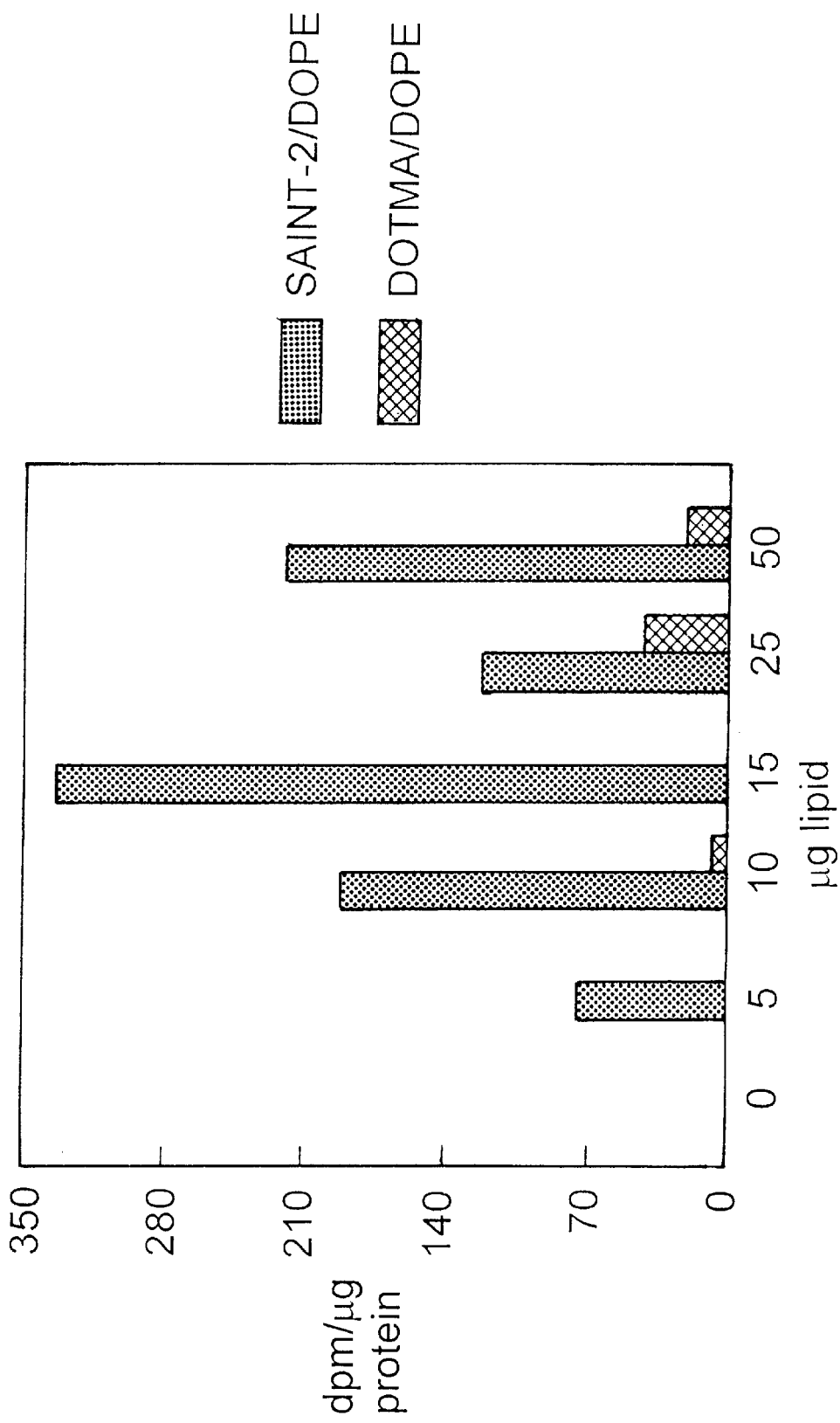
FIG. 2 is a graph showing the relative efficiencies of transfection of BHK cells using the synthetic amphiphile SAINT-2/DOPE or DOTMA/DOPE.
Figure 3:
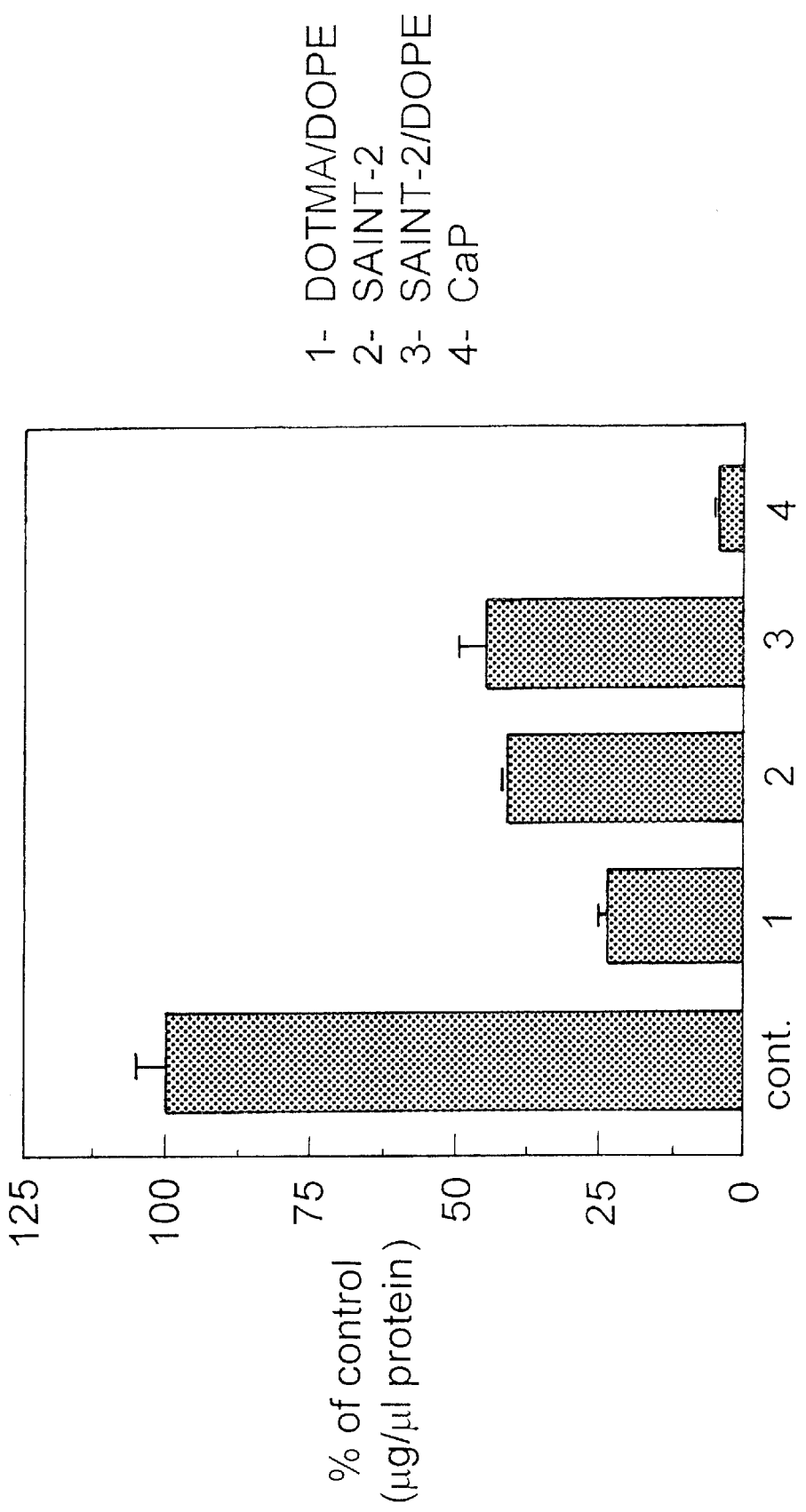
FIG. 3 is a graph showing the relative efficiencies of transfection of cells using the synthetic amphiphiles DOTMA/DOPE, SAINT-2, and SAINT-2/DOPE in comparison to transfection efficiency with calcium phosphate precipitation.

It appeared that with the new amphiphile also other cell types, including for instance BHK cells, can be transfected (FIG. 2). When a stable transfection is carried out with the new amphiphile it appeared to be possible to transfect 42–45% of the COS-7 cells. With DOTMA-DOPE vesicles on average 25–29% of the cells are transfected.

EXAMPLE 4

Transport of proteins in an eucaryotic cell

The synthetic amphiphile SAINT-2 is, in combination with DOPE, a suitable agent for the delivery of proteins into cells. The efficiency of protein internalisation with SAINT-2/DOPE as a carrier can be monitored with the aid of the gelonine protein. Internalized gelonine specifically inhibits the protein synthesis of cells and this inhibition is a direct measure for the amount of gelonine which has been brought into the cell. Unilamellar versicles of the synthetic agent amphiphile SAINT-2 and DOPE are obtained by bath sonication. Gelonine is added to a certain concentration (0–20 μM) SAINT-2/DOPE in HBS from a stock solution (2 mg/ml).

CV-1 cells, grown in twelve-well plates, are washed three times with HBS. Subsequently, the cells are incubated for 1 hour at 37° C. with the amphiphile/gelonine complex in BS obtained in this way. After this the cells are again washed three times with HBS.

The inhibition of protein synthesis by gelonine is being followed by determining the building-in of radioactively labelled methionine into the treated cells. This is carried out by incubating the cells for 30 minutes with 1 μCi$^{35}$S- methionine. Subsequently, the cells are washed three times with PBS and finally scraped in 10% TCA. The cell lysate obtained in this way is washed three times with 10% TCA and the amount of radioactive methionine present in the cell lysate is determined with the aid of a scintillation counter.

Incubation of CV-1 cells with the amphiphile/gelonine complex gives a strong inhibition of the protein synthesis with respect to the control experiment in which the cells were incubated with the synthetic amphiphile only. At a concentration of 5 μM SAINT-2/DOPE and 1.6 μM gelonine an inhibition of protein synthesis of 50% was obtained.

EXAMPLE 5

Toxicity studies

To determine the toxicity of the compound SAINT-2 according to the invention with respect to DOTMA-DOPE the COS-7 cells are incubated with different concentrations of both lipid samples. The residual protein content is taken as a measure for the amount of surviving cells.

A decrease of the protein content from 2 to 1 mg/ml was observed for DOTMA-DOPE starting from 71 μM lipid. For SAINT-2 a decrease from 2 to 1.75 mg/ml was found starting from 90 μM.

This shows that SAINT-2 is clearly less toxic than DOTMA-DOPE.

We claim:

1. A compound with the general formula I

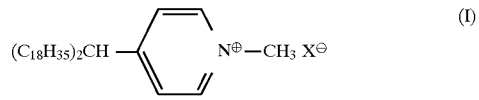

in which: X is selected from the group consisting of $Cl^-$, $Br^-$ and $I^-$.

2. A composition to introduce macromolecules into cells, comprising a mixture of a compound according to claim 1 and at least one macromolecule.

3. The composition according to claim 2, further comprising at least one targeting molecule.

4. The composition according to claim 3, wherein the targeting molecule is an antibody.

5. The composition according to claim 4, wherein the antibody is radioactively labeled or labeled with streptavidine.

6. The composition according to claim 2, wherein the macromolecule is a nucleic acid.

7. A method of introducing macromolecules into cells comprising:
   a. forming a mixture comprising a compound according to claim 1 and at least one macromolecule; and
   b. contacting cells with said mixture.

* * * * *